(12) United States Patent
Summers

(10) Patent No.: US 6,422,912 B1
(45) Date of Patent: Jul. 23, 2002

(54) NOVELTY ITEM WITH USER ACTUATED NOISE MAKER

(76) Inventor: Ethan Summers, 5512 Landmark Dr., Charlotte, NC (US) 28270

( * ) Notice: Subject to any disclaimer, the term of this patent is extended or adjusted under 35 U.S.C. 154(b) by 0 days.

(21) Appl. No.: 09/627,378

(22) Filed: Jul. 28, 2000

Related U.S. Application Data

(60) Provisional application No. 60/146,960, filed on Aug. 3, 1999.

(51) Int. Cl.[7] ................................................. A63H 3/28
(52) U.S. Cl. ........................ 446/184; 446/176; 446/193; 446/73
(58) Field of Search ................................. 446/176, 180, 446/183, 184, 188, 192, 193, 197, 475, 73

(56) References Cited

U.S. PATENT DOCUMENTS

| | | | |
|---|---|---|---|
| 3,691,675 A | * 9/1972 | Rodgers | 446/188 |
| 3,846,933 A | * 11/1974 | Hill et al. | 446/178 |
| 4,114,501 A | * 9/1978 | Tanaka | 446/193 |
| 4,149,338 A | * 4/1979 | Wolf | 446/186 |
| 4,160,338 A | * 7/1979 | Lyons et al. | 446/184 |
| 4,212,132 A | * 7/1980 | Lewanoni | 446/185 |
| 4,271,744 A | * 6/1981 | Kulesza | 446/193 |
| 4,447,250 A | * 5/1984 | Wolens et al. | 446/202 |
| 4,734,074 A | * 3/1988 | Kinberg et al. | 446/184 |
| 4,828,176 A | * 5/1989 | Crowe | 446/222 |
| 5,110,316 A | * 5/1992 | Shaw et al. | 446/202 |
| 5,261,850 A | * 11/1993 | Barthold | 446/193 |
| 5,310,380 A | * 5/1994 | Levy et al. | 446/489 |
| 5,522,756 A | * 6/1996 | Barthold | 446/193 |
| 5,873,766 A | * 2/1999 | Burton | 446/421 |
| 6,089,947 A | * 7/2000 | Green | 446/268 |

* cited by examiner

Primary Examiner—Jacob K. Ackun
Assistant Examiner—Faye Francis
(74) Attorney, Agent, or Firm—Adams, Schwartz & Evans, P.A.

(57) ABSTRACT

A novelty item includes a deformable hollow body having an air intake opening and an air exhaust opening. A scented article is contained in the hollow body between the intake and exhaust openings. A noise maker is attached to the body, and cooperates with a discharge of air through the exhaust opening upon deformation of the hollow body to produce a noise. The discharge of air has a scent corresponding to that of the scented article contained in the hollow body.

5 Claims, 6 Drawing Sheets

NOVELTY ITEM WITH USER ACTUATED NOISE MAKER

CLAIM OF BENEFIT OF EARLIER-FILED PROVISIONAL APPLICATION

This application claims the benefit of an earlier-filed provisional application entitled "Children' Toys", filed on Aug. 3, 1999, Serial No. 60/146,960.

TECHNICAL FIELD AND BACKGROUND OF INVENTION

This invention relates to a novelty item. The invention is entertaining and especially adapted for use and enjoyment by young children. The invention is easy to operate and relative inexpensive to manufacture. When actuated, the invention creates an expulsion of air which produces an amusing noise and odor. In one application, the invention includes a unique character with a face and body suitably colored and marked to be readily identified with a particular fruit. For example, the character "Smell'n Melon" illustrated in the drawings would produce a watermelon odor. Other fruit characters would produce odors corresponding to their own distinct candy fruit scent.

SUMMARY OF THE INVENTION

Therefore, it is an object of the invention to provide an entertaining novelty item for use and enjoyment by young children.

It is another object of the invention to provide a novelty item which is easy to operate.

It is another object of the invention to provide a novelty item which is relatively inexpensive to manufacture.

It is another object of the invention to provide a novelty item which is adapted for storing pieces of candy.

These and other objects of the present invention are achieved in the preferred embodiments disclosed below by providing a novelty item which includes a deformable hollow body having an air intake opening and an air exhaust opening. A scented article is contained in the hollow body between the intake and exhaust openings. A noise maker is attached to the body, and cooperates with a discharge of air through the exhaust opening upon deformation of the hollow body to produce a noise. The discharge of air has a scent corresponding to that of the scented article contained in the hollow body.

According to another preferred embodiment of the invention, the hollow body includes bellows adapted for alternate expansion and contraction to draw air in through the intake opening of the hollow body, and to discharge air outwardly from the hollow body through the exhaust opening.

According to another preferred embodiment of the invention, the hollow body defines a character face having eyes, a nose, and a mouth.

According to another preferred embodiment of the invention, the hollow body includes a base adapted for supporting the novelty item on a flat surface.

According to another preferred embodiment of the invention, the base defines a pair of character feet.

According to another preferred embodiment of the invention, the noise maker includes a rubber tube having a proximal end attached at the exhaust opening of the hollow body, and a flat distal end adapted for creating noise upon discharge of air outwardly through the tube.

According to another preferred embodiment of the invention, a rigid stem is attached to the hollow body, and extends adjacent the rubber tube for augmenting the noise created by the rubber tube upon discharge of air outwardly from the hollow body.

According to another preferred embodiment of the invention, the scented article includes a foam disc impregnated with a desired scent.

According to another preferred embodiment of the invention, an air intake valve assembly is located at the intake opening of the hollow body.

According to another preferred embodiment of the invention, a candy storage compartment is formed inside the hollow body and is adapted for receiving and storing candy.

According to another preferred embodiment of the invention, the candy storage compartment is sealed to prevent entry of air passing through the hollow body from the intake opening to the exhaust opening.

According to another preferred embodiment of the invention, an access opening is formed in the hollow body and provides access to the candy storage compartment.

According to another preferred embodiment of the invention, a hinged cap is provided for selectively opening and closing the access opening to the candy storage compartment.

In another embodiment, the invention is a novelty item including a deformable hollow body having an air intake opening and an air exhaust opening, a head and bellows. The bellows are adapted for alternate expansion and contraction to draw air in through the intake opening of the hollow body, and to discharge air outwardly from the hollow body through the exhaust opening. A scented article is contained in the hollow body and positioned between the head and bellows. A noise maker is attached to the hollow body, and cooperates with a discharge of air through the exhaust opening upon deformation of the hollow body to produce a noise. The discharge of air having a scent corresponding to that of the scented article contained in the hollow body.

According to another preferred embodiment of the invention, a candy storage compartment is formed inside the head of the hollow body and is adapted for receiving and storing candy.

According to another preferred embodiment of the invention, the candy storage compartment is sealed to prevent entry of air passing through the hollow body from the intake opening to the exhaust opening.

According to another preferred embodiment of the invention, a scented article storage compartment is located adjacent the candy storage compartment and between the head and bellows of the hollow body for storing the scented article. The scented article storage compartment is open for exposing the scented article to the passage of air into and through the hollow body.

BRIEF DESCRIPTION OF THE DRAWINGS

Some of the objects of the invention have been set forth above. Other objects and advantages of the invention will appear as the description proceeds when taken in conjunction with the following drawings, in which.

DESCRIPTION OF THE PREFERRED EMBODIMENT AND BEST MODE

Figure 1:
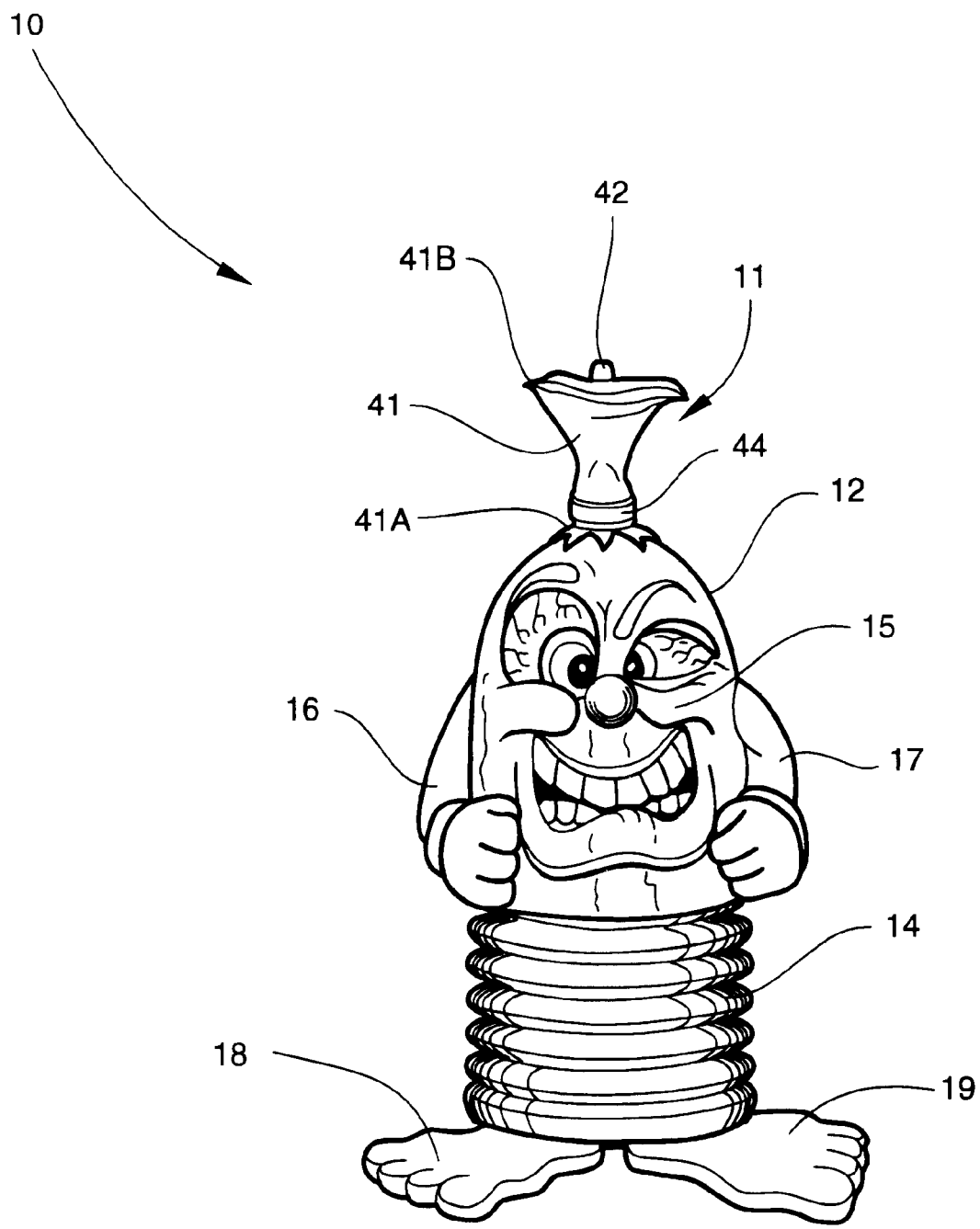
FIG. 1 is a front view of a novelty item according to one preferred embodiment of the present invention.
Figure 2:
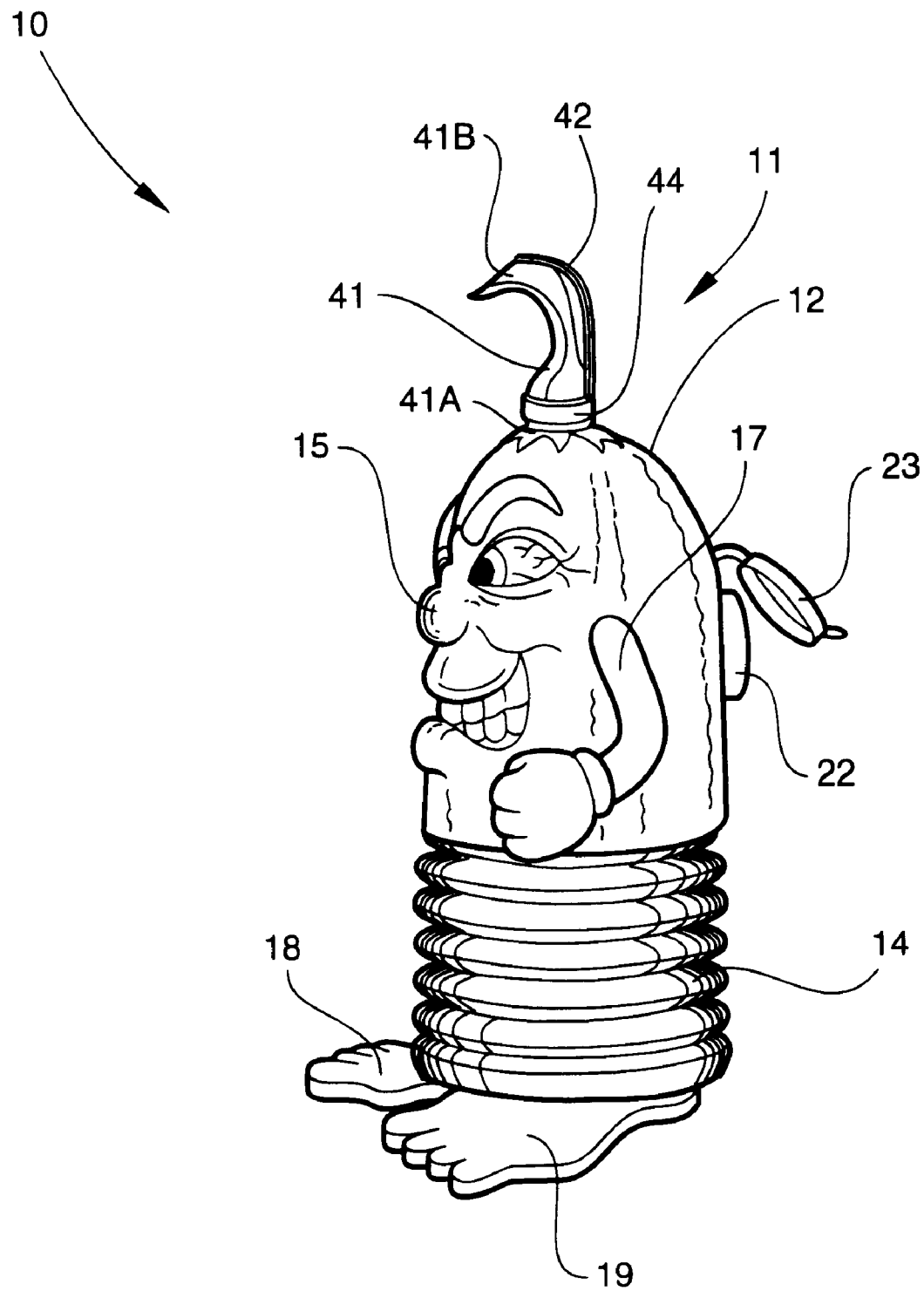
FIG. 2 is a side view of the novelty item.
Figure 3:
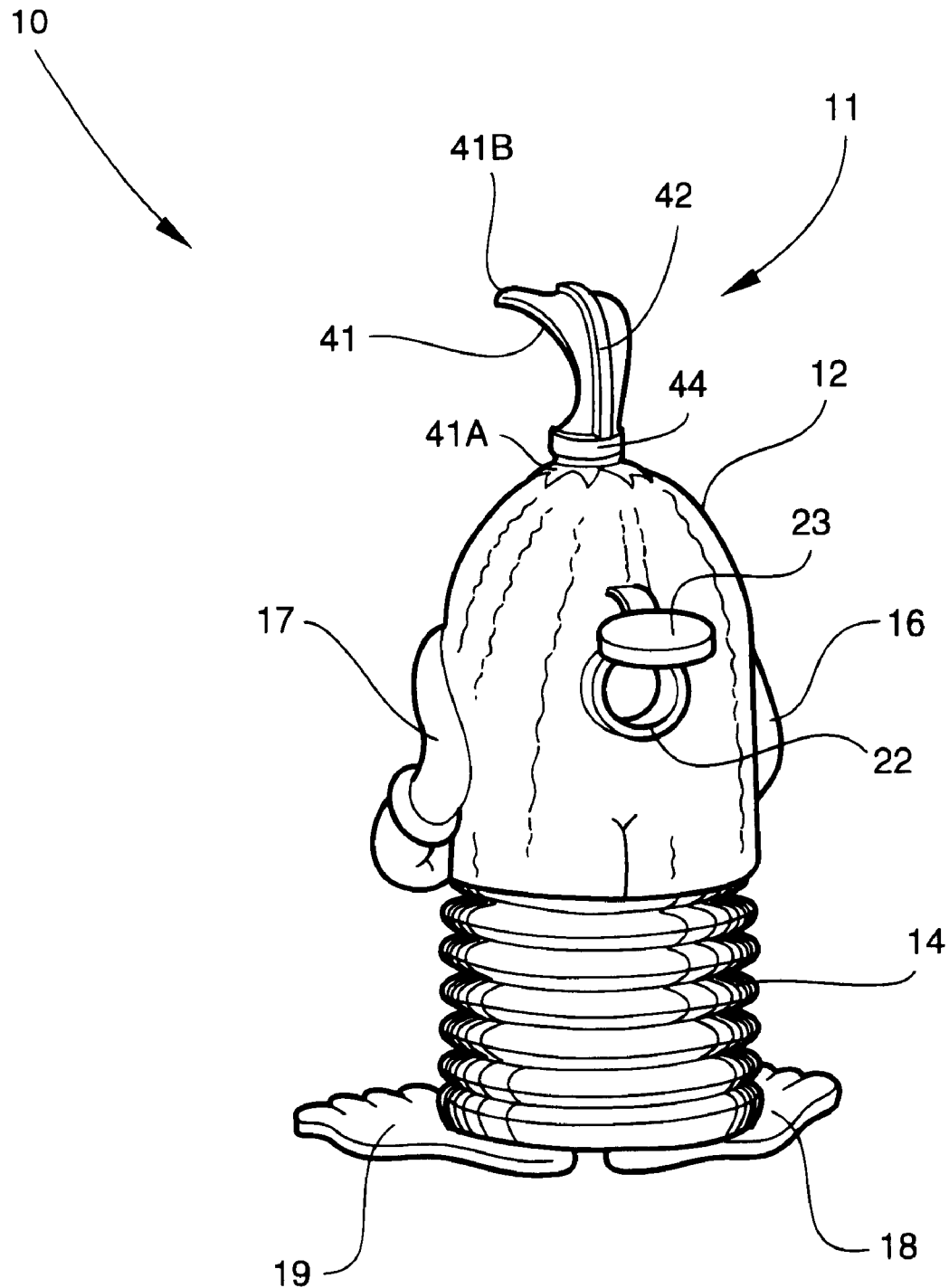
FIG. 3 is a rear view of the novelty item.
Figure 5:
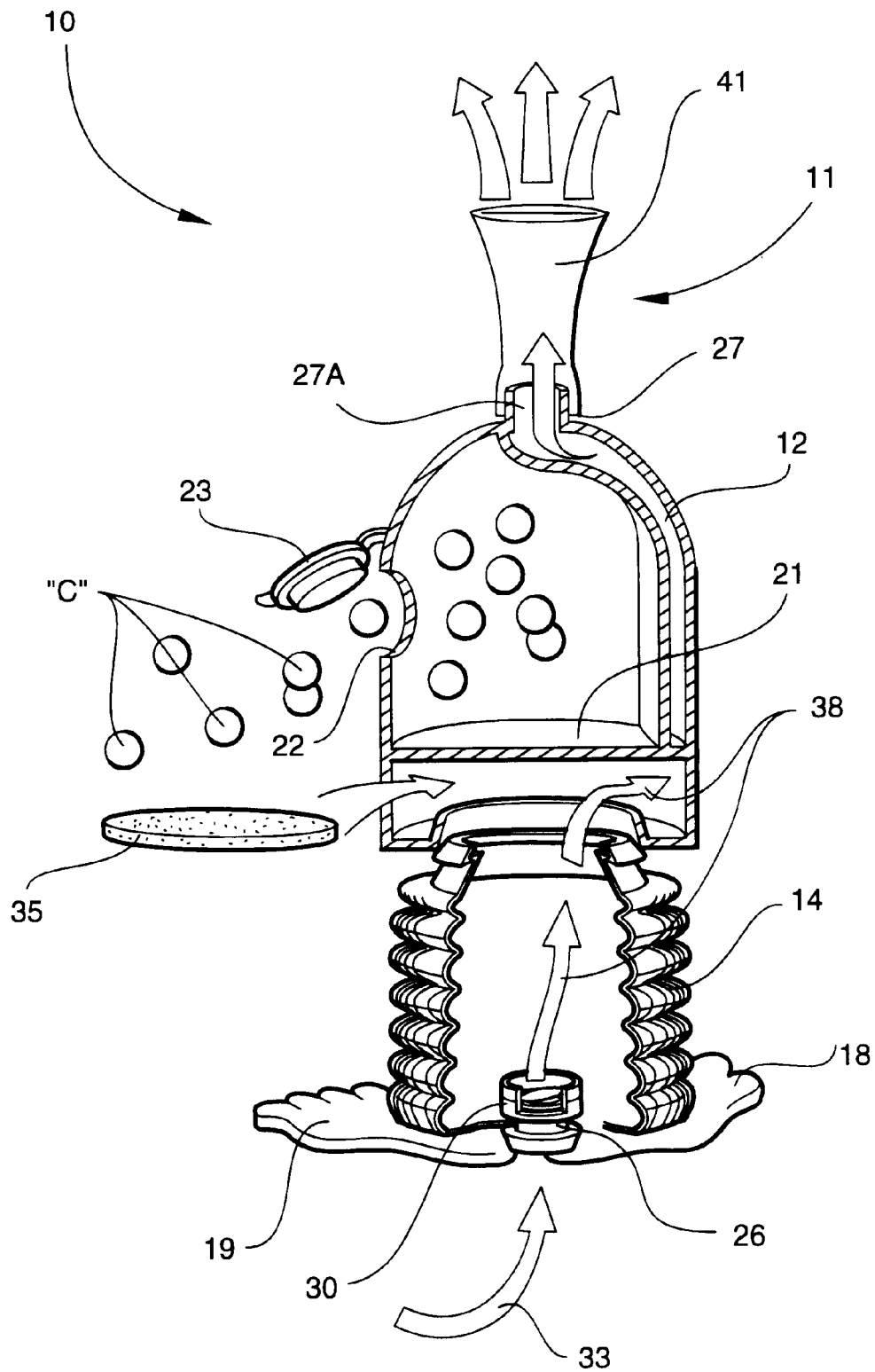
FIG. 5 is a cross-sectional view of the novelty item illustrating the flow of air into and through the hollow body of the item.

Referring now specifically to the drawings, a novelty item according to the present invention is illustrated in FIG. 1 and shown generally at reference numeral 10. In one embodiment of the invention, the novelty item 10 represents a character suitably colored and marked to be readily identified with a particular fruit. As best shown in FIGS. 1, 2, and 3, the novelty item 10 includes a noise maker 11, an attached head 12 and bellows 14, a face 15, two arms 16 and 17, and two feet 18 and 19. The feet 18 and 19 form a flat and stable base for locating the novelty item 10 on a flat surface. The unique character face 15 includes eyes, a nose, and a mouth. A candy storage compartment 21, shown in FIG. 5, is located inside the hollow head 12 of the item 10 and is accessible for receiving bits of candy "C" through an access opening 22 formed in the head 12. A hinged cap 23 permits opening and closing of the access opening 22.

Figure 4:
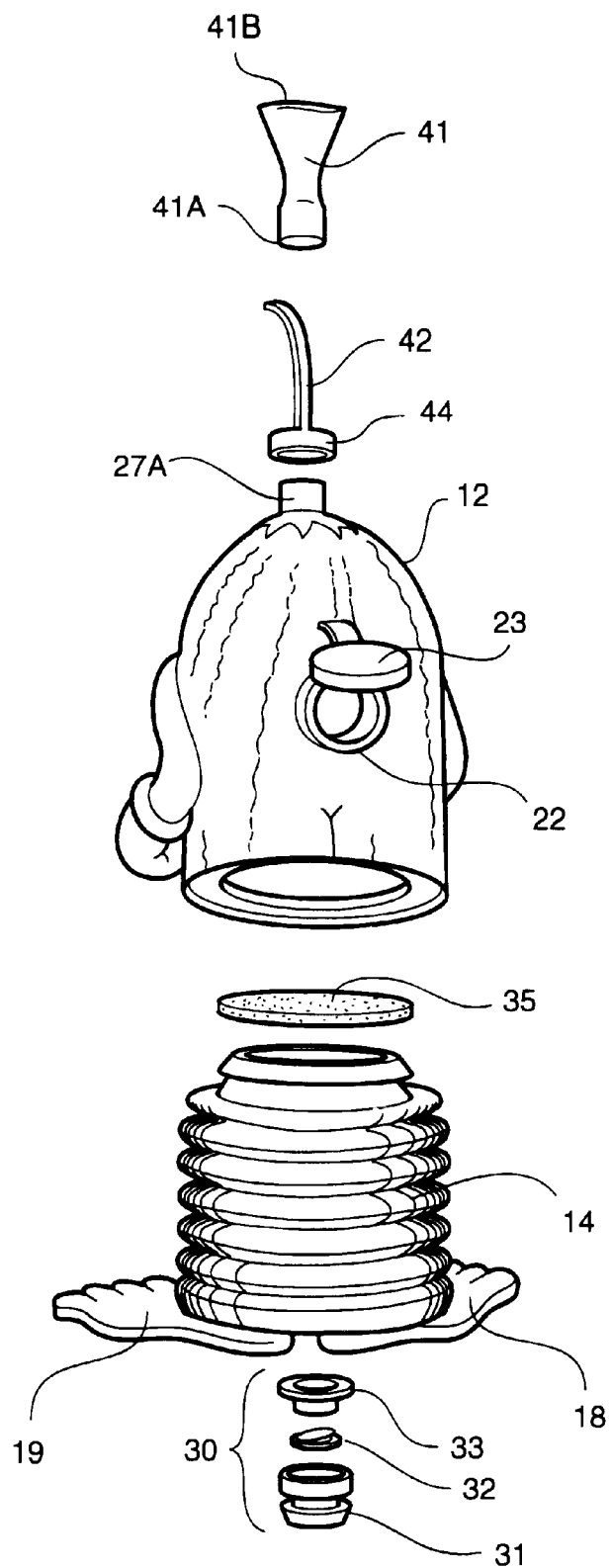
FIG. 4 is a rear exploded view of the novelty item.

As best shown in FIGS. 4 and 5, an air intake valve assembly 25 is located at an intake opening 26 formed in a bottom wall of the bellows 14 to permit air flow into and through the hollow body of the item 10, and outwardly through an exhaust opening 27 formed in the head 12. The intake valve assembly 30 includes an open-ended housing 31 with an inside annular shoulder, an intake valve 32 positioned within the housing 31 adjacent the inside shoulder, and an open-ended retaining plug 33 for holding the valve 32 inside the housing 31.

A fruit-scented, non-toxic foam disc 35 is positioned in an open storage compartment 36 located between the candy storage compartment 21 and the connecting ends of the head 12 and bellows 14. The path of air flow into and through the intake valve assembly 30, the bellows 14, the scented foam disc 35 and hollow head 12 is indicated by arrows 38 shown in FIG. 5. After passing through the scented disc 35, the resulting "scented" air exits the head 12 through the exhaust opening 27. Preferably, the interior of the candy storage compartment 21 is sealed to prevent dissipation of scented air into this compartment.

The noise maker 11 is attached at the exhaust opening 27 formed in the head 12, and functions to create noise upon discharged of the scented air outwardly from the hollow body of the item 10. In one embodiment, the noise maker 11 is a rubber tube 41 with a proximal end 41A secured over a raised mouth 27A of the exhaust opening 27, and a relatively flat and wide distal end 41B. A generally rigid stem 42 with an annular base 44 fits onto the raised mouth 27A and over the proximal end 41A of the rubber tube 41 to further secure the rubber tube 41 to the head 12. The stem 42 augments the noise created by the rubber tube 41 upon reverberation of the flat distal end 41B caused by the discharge of scented air outwardly through the exhaust opening 27.

Figure 6:
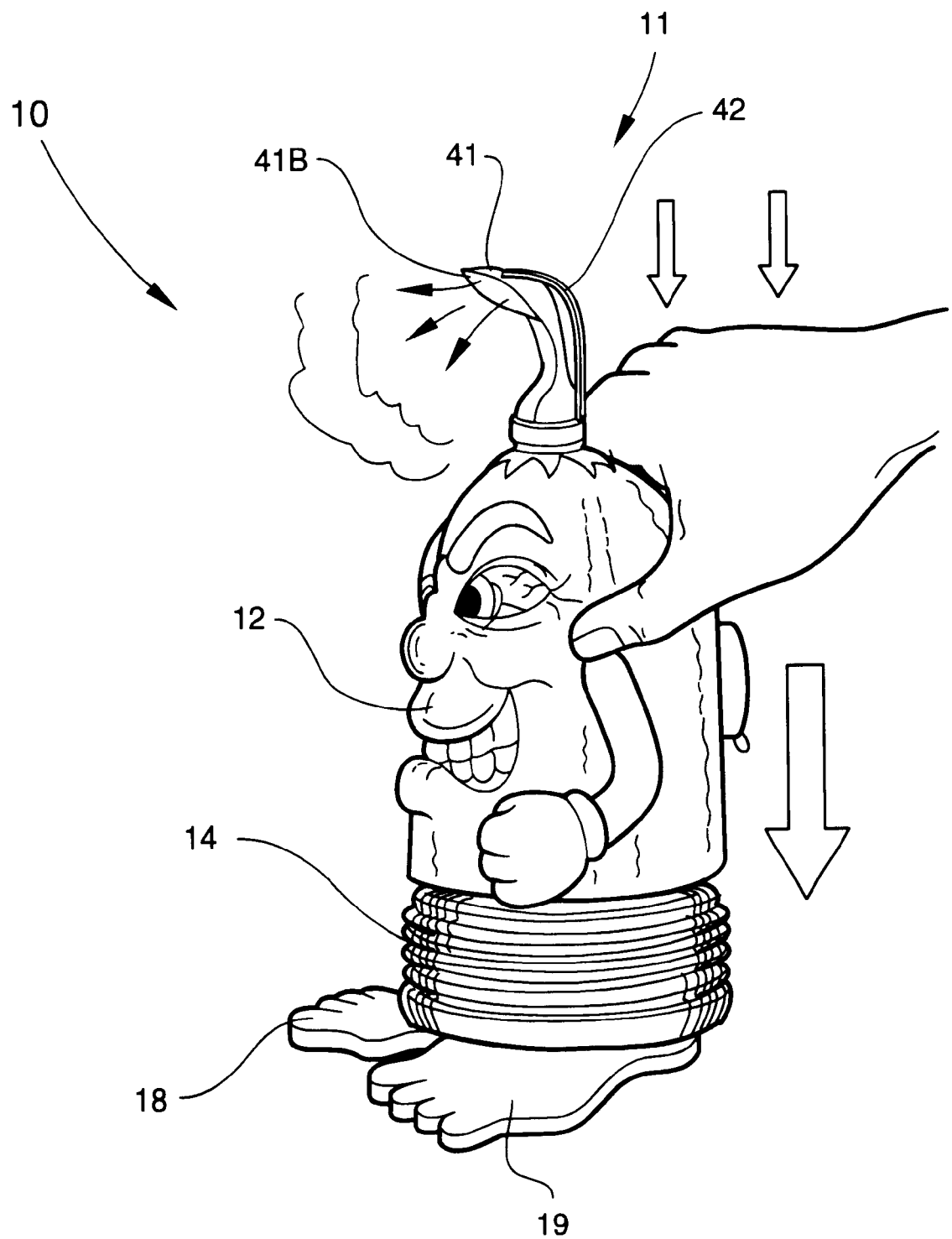
FIG. 6 is a view demonstrating operation of the novelty item with the bellows in the compressed condition, and scented air discharged outwardly through the noise maker.

Operation of the novelty item 10 is demonstrated in FIG. 6. With the item 10 placed upright on a flat surface and the bellows 14 in an extended condition, the user grasps the head 12 and urges it downwardly. This action compresses the bellows 14, as shown, and forces air outwardly from the hollow body of the item 10 through the exhaust opening 27 and noise maker 11. The expulsion of scented air through the distal end 41B of the rubber tube 41 creates a simultaneous and entertaining noise intending to resemble the sound of flatulence. To reset the item 10, the bellows 14 are pulled back to their expanded condition and the air intake valve assembly 30 permits re-entry of air into the hollow body of the item 10.

A novelty item is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:
1. A novelty item comprising:
   (a) a deformable hollow body having an air intake opening and an air exhaust opening, and comprising a head and bellows, the bellows being adapted for alternate expansion and contraction to draw air in through the intake opening of said hollow body, and to discharge air outwardly from said hollow body through the exhaust opening, and the head of said hollow body defining a character face having eyes, a nose, and a mouth;
   (b) a scented article contained in said hollow body and positioned between the head and bellows; and
   (c) a noise maker comprising a rubber tube having a proximal end attached at the exhaust opening of said hollow body, and a flat distal end adapted for creating a reverberating noise upon deformation of said hollow body to discharge air outwardly through said tube, said discharge of air having a scent corresponding to that of the scented article contained in said hollow body.

2. A novelty item according to claim 1, and comprising a candy storage compartment formed inside the head of said hollow body and adapted for receiving and storing candy.

3. A novelty item according to claim 2, wherein said candy storage compartment is sealed to prevent entry of air passing through said hollow body from the intake opening to the exhaust opening.

4. A novelty item according to claim 3, and comprising a scented article storage compartment located adjacent said candy storage compartment and between the head and bellows of said hollow body for storing said scented article, said scented article storage compartment being open for exposing said scented article to the passage of air into and through said hollow body.

5. A novelty item according to claim 1, and comprising an air intake valve assembly located at the intake opening of said hollow body.

\* \* \* \* \*